(12) United States Patent
Deak et al.

(10) Patent No.: US 10,232,109 B2
(45) Date of Patent: Mar. 19, 2019

(54) MINI LEAD SCREW PUMP UTILIZING A MAGNETORESISTIVE SENSOR AND MANUFACTURING METHOD THEREOF

(71) Applicant: MultiDimension Technology Co., Ltd., Zhangjiagang (CN)

(72) Inventors: James Geza Deak, Zhangjiagang (CN); Yuqin Jin, Zhangjiagang (CN)

(73) Assignee: MultiDimension Technology Co., Ltd., Zhangjiagang. Jiangsu (CN)

( * ) Notice: Subject to any disclaimer, the term of this patent is extended or adjusted under 35 U.S.C. 154(b) by 17 days.

(21) Appl. No.: 15/304,251

(22) PCT Filed: Apr. 13, 2015

(86) PCT No.: PCT/CN2015/076428
§ 371 (c)(1),
(2) Date: Oct. 14, 2016

(87) PCT Pub. No.: WO2015/158230
PCT Pub. Date: Oct. 22, 2015

(65) Prior Publication Data
US 2017/0028124 A1 Feb. 2, 2017

(30) Foreign Application Priority Data

Apr. 14, 2014 (CN) .......................... 2014 1 0146550

(51) Int. Cl.
*A61M 5/145* (2006.01)
*A61M 5/168* (2006.01)
*A61M 5/172* (2006.01)

(52) U.S. Cl.
CPC .......... *A61M 5/145* (2013.01); *A61M 5/1452* (2013.01); *A61M 5/1684* (2013.01); *A61M 5/1723* (2013.01); *A61M 2205/3317* (2013.01)

(58) Field of Classification Search
CPC .................. A61M 2205/3317; A61M 5/14236
See application file for complete search history.

(56) References Cited

U.S. PATENT DOCUMENTS

| 4,435,173 A | 3/1984 | Siposs et al. |
| 8,382,703 B1 | 2/2013 | Abdelaal |

(Continued)

FOREIGN PATENT DOCUMENTS

| CN | 1266373 | 9/2000 |
| CN | 101745163 | 6/2010 |

(Continued)

OTHER PUBLICATIONS

"International Application No. PCT/CN2015/076428, International Search Report and Written Opinion dated Jun. 29, 2015", (Jun. 29, 2015), 13 pgs.

(Continued)

*Primary Examiner* — Deanna K Hall
(74) *Attorney, Agent, or Firm* — Schwegman Lundberg & Woessner, P.A.

(57) ABSTRACT

A mini lead screw pump monitors the rotation of a lead screw by using a magnetoresistive sensor and an MCU, and uses feedback to control the rotation direction and speed of the lead screw through a motor controller so as to control the speed of infusion to a patient. Furthermore, this mini lead screw pump can control the infusion speed of insulin according to the patient's blood sugar concentration monitored by CGM. This mini lead screw pump has several advantages, comprising high sensitivity, high reliability, low power consumption, low cost, and ease of use.

20 Claims, 4 Drawing Sheets

(56) References Cited

U.S. PATENT DOCUMENTS

| | | | |
|---|---|---|---|
| 9,677,555 B2* | 6/2017 | Kamen | F04B 43/1261 |
| 2002/0043951 A1 | 4/2002 | Moberg | |
| 2003/0233069 A1 | 12/2003 | Gillespie, Jr. et al. | |
| 2010/0050731 A1 | 3/2010 | Granig et al. | |
| 2010/0118447 A1 | 5/2010 | Hammerschmidt et al. | |
| 2010/0211003 A1* | 8/2010 | Sundar | A61M 5/16813 604/67 |
| 2011/0301566 A1 | 12/2011 | Schaefer | |
| 2013/0281965 A1 | 10/2013 | Kamen et al. | |
| 2017/0056581 A1 | 3/2017 | Deak et al. | |

FOREIGN PATENT DOCUMENTS

| | | |
|---|---|---|
| CN | 201692426 | 1/2011 |
| CN | 202113388 | 1/2012 |
| CN | 102614565 | 8/2012 |
| CN | 103191486 | 7/2013 |
| CN | 203163674 | 8/2013 |
| CN | 103656797 | 3/2014 |
| CN | 103768679 | 5/2014 |
| CN | 103920207 | 7/2014 |
| CN | 203802882 | 9/2014 |
| CN | 203885937 | 10/2014 |
| DE | 29622313 | 3/1997 |
| EP | 0390388 | 10/1990 |
| EP | 0465267 | 1/1992 |
| EP | 2682772 | 1/2014 |
| JP | H0584296 | 4/1993 |
| WO | WO-2004113928 | 12/2004 |
| WO | WO-2015124081 | 8/2015 |
| WO | WO-2015/158230 | 10/2015 |

OTHER PUBLICATIONS

"U.S. Appl. No. 15/119,689, Non Final Office Action dated Apr. 18, 2018", 10 pgs.

"Chinese Application No. 201410146550.4, First Office Action dated Aug. 18, 2015", (Aug. 18, 2015), 8 pgs.

"Chinese Application No. 201410146550.4, Second Office Action dated Feb. 26, 2016", (Feb. 26, 2016), 7 pgs.

"European Application No. 15780592.0, Extended European Search Report dated Nov. 15, 2017", (Nov. 15, 2017), 9 pgs.

"International Application No. PCT/CN2015/072868, International Search Report dated Apr. 29, 2015", (Apr. 29, 2015), 5 pgs.

"Chinese Application No. 201410058046.9, First Office Action dated Apr. 3, 2015", (Apr. 3, 2015), 8 pgs.

"Chinese Application No. 201410058046.9, Second Office Action dated Dec. 29, 2015", (Dec. 29, 2015), 8 pgs.

"European Application No. 15751470.4, Extended European Search Report dated Sep. 29, 2017", (Sep. 29, 2017), 6 pgs.

"U.S. Appl. No. 15/119,689, Response filed Jul. 18, 2018 to Non Final Office Action dated Apr. 18, 2018", 9 pgs.

* cited by examiner 2B    2C    2D

MINI LEAD SCREW PUMP UTILIZING A MAGNETORESISTIVE SENSOR AND MANUFACTURING METHOD THEREOF

PRIORITY CLAIM TO RELATED APPLICATIONS

This application is a U.S. national stage application filed under 35 U.S.C. § 371 from International Application Serial No. PCT/CN2015/076428, which was filed 13 Apr. 2015, and published as WO2015/158230 on 22 Oct. 2015, and which claims priority to Chinese Application No. 201410146550.4, filed 14 Apr. 2014, which applications and publication are incorporated by reference as if reproduced herein and made a part hereof in their entirety, and the benefit of priority of each of which is claimed herein.

TECHNICAL FIELD

The present invention relates to a medical device, and in particular, to a mini lead screw pump for driving an insulin pump.

BACKGROUND ART

As the number of diabetic patients increases globally, the demand for insulin pumps is also increasing. An insulin pump needs to inject insulin at a low dosage at a constant rate or a large dosage according to the requirements of a diabetic patient to correct high blood sugar after a meal is eaten. The insulin pump can inject insulin according to a basic dosage distribution diagram of the diabetic patient, and therefore, the blood sugar concentration in the blood of the patient can be kept at the same level, and organs of the patient bear less pressure. Accordingly, the insulin pump must be capable of injecting insulin at a small dosage (about 0.1-1.0 cm$^3$/day) continuously, and be capable of adjusting the speed of injection (that is, the basic dosage speed and the large dosage speed) in a wide range, to meet different requirements of patients. As a result, many insulin pumps available in the market are mini lead screw pumps; the mini lead screw pump drives a sleeve to move within a reservoir, to input the insulin inside the reservoir into the body of the patient. A motor for rotating the lead screw may be a stepper motor that can control the rotation speed precisely. On one hand, using the stepper motor increases the price of the insulin pump, the price of this type of insulin pump may be up to 5000 dollars, which greatly limits the use by patients. On the other hand, the precision of the stepper motor controlling the infusion speed depends on the number of phases and the number of beats, and the more the number of phases and the number of beats are, the higher the precision is. Low-frequency vibration easily occurs when the stepper motor rotates at a low speed. Step loss or locked rotor easily occurs at an over-high start-up frequency or overly high load, and overshoot may occur if the rotation speed is too high when the motor stops. In order to reduce the price of the insulin pump, the present invention uses a magnetoresistive angle sensor and a DC motor together to replace the stepper motor, thereby reducing the cost of the insulin pump, and improving the performance of the insulin pump.

SUMMARY OF THE INVENTION

The present invention relates to a mini lead screw for driving an insulin pump, which uses feedback to control the infusion speed by using a magnetoresistive angle sensor and a continuous glucose monitor (CGM) in combination with a micro control unit (MCU), and replaces the manner of controlling the infusion speed by using a stepper motor. The present invention can use other motors to replace the stepper motor, and may also be used with the stepper motor, thereby improving the precision and reliability of the infusion speed of insulin or other liquid.

A mini lead screw pump, mounted within a pump box, the mini lead screw pump comprising a motor, the motor driving the lead screw and a driving head connected to the lead screw, the lead screw rotating in a nut having a thread in a direction opposite to that of a thread of the lead screw, thereby driving the driving head to push a sleeve to move within a reservoir, where the mini lead screw pump further comprises at least one permanent magnet rotating co-axially with the lead screw;

a magnetoresistive angle sensor capable of sensing a magnetic field generated by the at least one permanent magnet, the magnetoresistive angle sensor being located within a unidirectional and saturated area of the magnetic field generated by the at least one permanent magnet; and an MCU receiving a signal of the magnetoresistive angle sensor and using feedback to control the rotation direction and speed of the lead screw according to the signal of the magnetoresistive angle sensor.

Preferably, the magnetoresistive angle sensor is a biaxial magnetic angle sensor, two orthogonal uniaxial magnetic angle sensors, or a uniaxial or biaxial linear magnetic sensor.

Preferably, the magnetoresistive angle sensor is an AMR, a GMR or a TMR sensor.

Preferably, the central axis of the permanent magnet and the central axis of the lead screw pass through the center of the magnetoresistive angle sensor.

Preferably, the at least one permanent magnet is a one-piece permanent magnet or a split-type permanent magnet, and is disc-shaped, ring-shaped or square-shaped.

Preferably, the at least one permanent magnet is two permanent magnets, each of the permanent magnets has multiple different magnetic poles, and the two permanent magnets are located at two ends of the lead screw respectively or disposed at the same end of the lead screw as a string.

Preferably, the MCU controls the rotation direction and speed of the motor through a motor controller.

Preferably, the MCU comprises a magnetoresistive sensor information management unit, the magnetoresistive sensor information management unit comprises a motor angle counting unit for monitoring the angle of the motor, a lead screw position unit for calculating a linear movement position of the lead screw and/or a sleeve position unit for calculating a position of the sleeve in the reservoir, a solution volume unit for calculating the volume of a solution in the reservoir, and a flow velocity unit for converting the rotation speed of the lead screw into the infusion speed of the reservoir.

Preferably, the MCU has a wired and/or wireless data communication interconnecting function.

Preferably, the MCU receives a signal sent by a CGM connected thereto, and calculates an actually required infusion speed according to a CGM look-up table preset in the MCU.

Preferably, the mini lead screw pump comprises a comparison unit for comparing the infusion speed of the mini lead screw pump and the actually required infusion speed, and the MCU adjusts the rotation speed of the lead screw according to comparison data feedback of the comparison unit.

Preferably, the motor is a DC motor or a stepper motor.

Preferably, a transmission device connecting the motor and the lead screw is included.

Preferably, a slideway or a guide rod is included, the slideway or guide rod is parallel to the lead screw, and the driving head slides within the slideway or slides along the guide rod.

Preferably, an anti-backlash device located on the lead screw is included.

A method for manufacturing a mini lead screw pump described above, the mini lead screw pump comprising a lead screw and a driving head connected to the lead screw, and the lead screw rotating clockwise or counterclockwise, thereby driving the driving head to push a sleeve to move within a reservoir, wherein the method comprises:

mounting at least one permanent magnet on the lead screw such that it is rotatable co-axially with the lead screw, and mounting a magnetoresistive angle sensor at a position within a unidirectional and saturated area of a magnetic field generated by the at least one permanent magnet; and mounting an MCU for using feedback to control the rotation direction and speed of the lead screw according to a signal of the magnetoresistive angle sensor.

Preferably, the magnetoresistive angle sensor is an AMR, a GMR or a TMR sensor.

According to the present invention, a common DC motor is used instead of an expensive stepper motor, thus reducing the cost of an insulin pump. Moreover, the application of the low-power consumption magnetoresistive angle sensor may also reduce the power consumption of the insulin pump and reduce the frequency of charging, which is an important improvement for an insulin pump generally powered by batteries, thereby facilitating the use. In conclusion, the insulin pump of the present invention has several advantages, including high sensitivity, high reliability, low power consumption, low cost, and ease of use.

DETAILED DESCRIPTION

The above description is merely a summary of the technical solution of the present invention. In order to describe the technical measures of the present invention more clearly and implement the present invention according to the content of the specification, the present invention will be described in detail below with reference to embodiments and accompanying drawings. Specific implementations of the present invention are provided in detail by the following embodiments.

Figure 1:
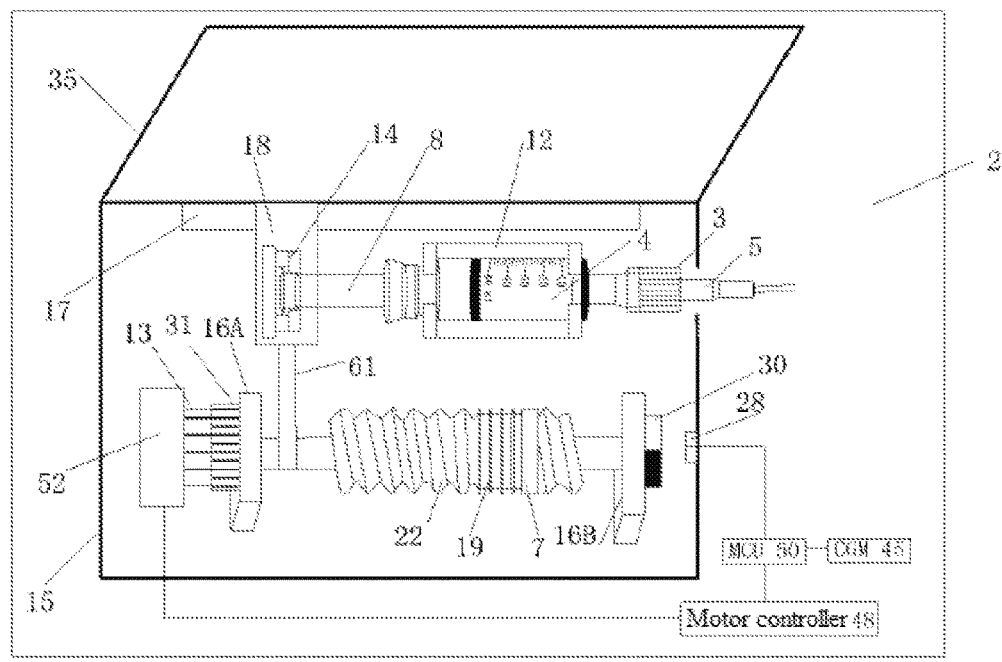
FIG. 1 is a schematic top view of an insulin pump.

FIG. 1 is a schematic top view of a mini lead screw pump or an insulin pump 2. The pump comprises a motor 52, a lead screw 22 and a driving head 18 driven by the motor 52, and is mounted within a pump box 15. The pump box 15 has a box cover 35. A reservoir 4 has a sleeve 8 capable of moving therein. A locking connector 3 (Luer lock) connects the reservoir 4 and a connector 5 of an infusion tube, and the connector 5 of the infusion tube is connected to a hose for infusing insulin to the body of a patient.

One end of the lead screw 22 connected to the motor 52 is rotatably fixed to a front base 16A, and the other end is rotatably fixed to a rear base 16B. In order to drive the driving head 18, the lead screw 22 is connected to the driving head 18 through a linkage rod 61 so as to convert the rotation thereof to the translation of the driving head 18, and can rotate in a nut 7 having an internal thread matched with an external thread of the lead screw 22. The nut 7 is fixed to the pump box 15. Through a mechanical transmission device capable of changing the rotation speed, including one or more reduction gears 13 and gears 31, the motor 52 drives the lead screw 22 to rotate in the nut 7 clockwise or counterclockwise. Therefore, the lead screw 22 drives the driving head 18 to move back and forth linearly along a direction parallel to the slideway 17. The slideway 17 is a groove allowing the driving head 18 to slide therein, and is parallel to the lead screw 22. To reduce cost, a pulley and a transmission belt may be used to replace the gear 31 and the reduction gear 13 between the motor 52, the reduction gear 13 and the gear 31. An anti-backlash device 19 is mounted on the lead screw 22 to prevent backlash.

The slideway 17 may not be used, but a guide rod is used for stabilization and guiding, and the guide rod is parallel to the lead screw 22. The number of guide rods for stabilization may be one or more.

The motor 52 may be a DC motor, an AC motor, a stepper motor, a servo motor, or the like.

The mini lead screw pump further comprises a magnetoresistive angle sensor 28 and at least one permanent magnet 30 rotating co-axially with the lead screw 22, wherein the magnetoresistive angle sensor 28 is stationary and can sense a magnetic field generated by the permanent magnet 30.

The driving head 18 has a pair of reservoir clips 14 capable of fixing reservoirs 4 with different diameters to the same injector central axis or different injector central axes, to hold the sleeve 8; therefore, when the lead screw 22 rotates in the nut 7, the driving head 18 moves linearly along the direction of the slideway 17, thereby pushing the sleeve 8 to move in the reservoir 4. The pump box 15 is provided with a pair of syringe clips 12, which can fix reservoirs 4 with different diameters to the same injector central axis or different injector central axes.

Figure 2:
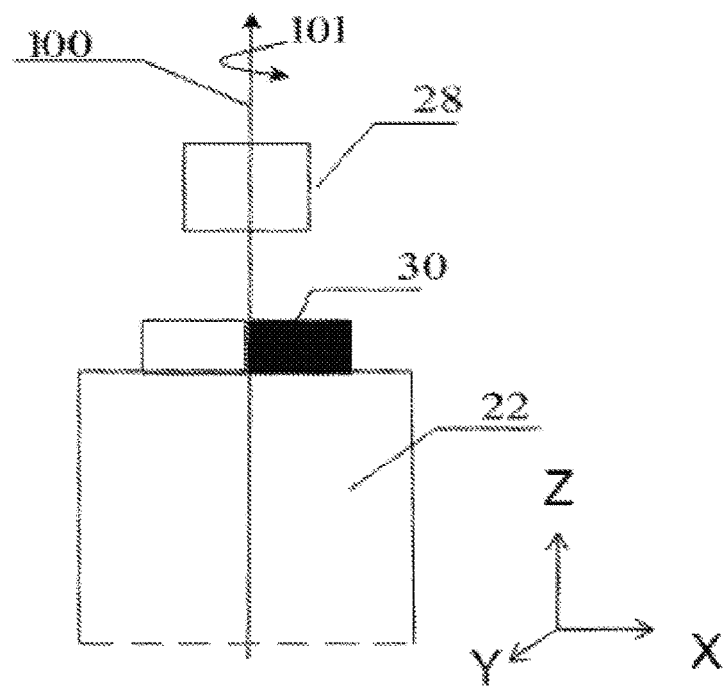
FIG. 2 is a schematic diagram of a permanent magnet and the magnetization direction thereof.
Figure 2:
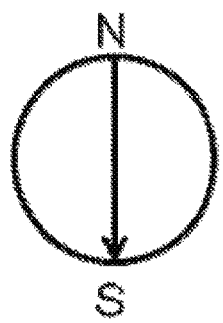
Figure 2:
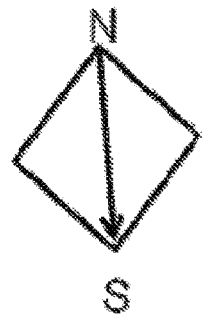
Figure 2:
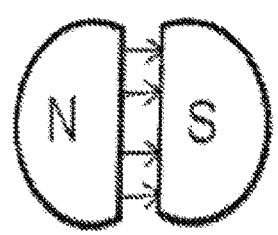

FIG. 2A is a schematic sectional diagram of a positional relation between the magnetoresistive angle sensor 28 and the permanent magnet 30 and FIG. 2B to FIG. 2D are schematic diagrams of the magnetization direction of the permanent magnet 30. The lead screw 22 has a long axis 100 in the direction of Z-axis direction, which is perpendicular to XY plane, passes through the center of the permanent magnet 30, and is coaxial with the permanent magnet 30. The central axis of the permanent magnet 30 and the central axis of the lead screw 22 pass through the center of the magnetoresistive angle sensor 28. The magnetoresistive angle sensor 28 is a biaxial magnetic angle sensor or two orthogonal uniaxial rotary sensors, and may also be a linear sensor or a biaxial linear sensor. The magnetoresistive angle sensor 28 is an AMR, a GMR, or a TMR sensor. FIG. 2B, FIG. 2C and FIG. 2D show a part of permanent magnets applicable to the present invention. The permanent magnet 30 is disc-shaped, ring-shaped or square-shaped, and is a one-piece permanent magnet or a split-type permanent magnet. The permanent magnet 30 may also comprise two magnets, and each permanent magnet has a different number of multiple magnetic poles. The surface area of the magnetoresistive angle sensor 28 on the XY plane is less than the coverage area of the permanent magnet 30 on the XY plane. The permanent magnet 30 is magnetized along the diameter or the diagonal direction, and the magnetization direction thereof is perpendicular to the Z-axis direction or the long-axis direction of the lead screw 22. The disc-shaped or ring-shaped permanent magnet is magnetized along the diameter direction, and the square-shaped permanent magnet is magnetized along the diagonal direction. The permanent magnet 30 may be located at one end of the lead screw 22 away from the motor 52, and may also be located at the same end with the motor 52. If the permanent magnet 30 comprises two magnets, the two permanent magnets are respectively located at two ends of the lead screw 22 or disposed at the same end of the lead screw 22 as a string. The permanent magnet 30 may be located near or away from the magnetoresistive angle sensor 28. If the two permanent magnets are disposed at the same end of the lead screw 22 as a string, the magnetoresistive angle sensor 28 may be located near or away from the lead screw. The magnetoresistive angle sensor 28 is located within a unidirectional and saturated area of the magnetic field of the permanent magnet 30.

Figure 3:
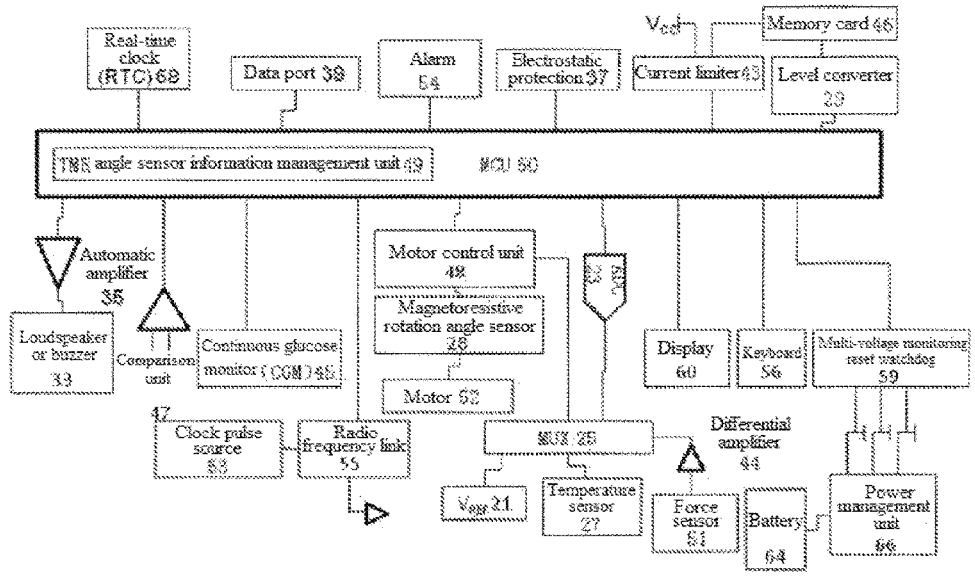
FIG. 3 is a control principle diagram of an MCU.

FIG. 3 is a control principle diagram of an MCU 50. The insulin pump 2 comprises the MCU 50, which receives a signal from the magnetoresistive angle sensor 28, and controls the rotation direction and speed of the motor 52 through a motor controller/motor control unit 48 connected thereto. Moreover, the MCU 50 is further connected with an operation keyboard 56, a display 60 and a battery 64. The display 60 and the keyboard 56 are located on the box cover 35.

The motor controller 48 is further used to monitor an output signal of the magnetoresistive angle sensor 28, and if the preset sleeve position and infusion speed are found, the motor controller 48 may activate an alarm 54 connected thereto.

The MCU 50 displays information that should be known by a user of the insulin pump 2 on the display 60. The user can also communicate with the insulin pump 2 by using the keyboard 56 connected to the MCU 50. The MCU 50 is connected to a force sensor 51, the force sensor 51 may detect a force applied to the reservoir 4, and when the force exceeds a preset value, the force sensor 51 may activate the alarm 54 through the motor controller 48. A typical design of the force sensor 51 is a bridge structure, which uses analog-digital conversion (ADCs) and a differential programmable gain to amplify input or uses ADCs and external differential equipment for signal adjustment for the amplification.

The battery 64 provides power required by an electrical device and the motor 52. The power display depends on a simple battery voltage or a temperature sensor 27. The reading of the voltage or temperature is digitized on an ADC 23. The MCU 50 may receive the digitized data, process the data, and determine the remaining power by using a pre-stored look-up table. The power is displayed on the display 60. When the power is too low, the alarm 54 may send an alarm.

A power management unit 66 connected to the battery 64 converts the battery to a low-power consumption state when the power supply is turned off or when the insulin pump 2 is not in use.

In a multi-voltage system, the simplest method of generating a power-up reset signal is monitoring a logic power source. During power up, the logic voltage rises above its threshold value, and a multi-voltage monitoring reset watchdog 59 connected to the power management unit 66 starts a reset stage, to ensure starting the MCU 50 sequentially. The multi-voltage monitoring reset watchdog 59 continues detecting any possible short-time power supply problem or power outage as long as the voltage of the power source of the host is within a specified specification. The existing multi-voltage monitoring reset watchdog 59 available in the market can monitor two, three or even four power supply voltages.

When the user inputs information, a visual or acoustic signal should be provided. The display 60 provides the dosage and infusion speed of insulin, remaining power, time and date, prompt and system alarm (that is, blocking or low remaining insulin). The display 60 may also provide information about self-test during power up. A sound player 33 must have a self-test function, and this self-test function can receive sound by indirectly monitoring the impedance of a micro speaker or placing a loudspeaker beside the micro speaker, to determine whether the sound is at an appropriate level. An automatic amplifier 35 connected to the sound player 33 is used to adjust the volume. The display 60 may be a touch screen. If the display 60 is a touch screen, it is preferably disposed at an inner side of the box cover 35.

The insulin pump 2 requires that a visual and acoustical alarm is provided when an error is found, a specified time is reached or any event to be alarmed occurs. The alarm 54 may send an alarm when the following event occurs: low power, battery failure, low insulin, no insulin in an insulin bottle, excessive insulin amount, pump pause, pump failure (there may be many different situations), blocking and the like. A single LED may also be used to display an operating state of the insulin pump 2, where red indicates an abnormal state, and green indicates a normal state.

An electrostatic protection 37 is implemented by using an electronic device with built-in protection or using an electrostatic discharge (ESD) line protection.

A data port 39 allows data transfer and downloading upgrade software, and also allows inputting a historical file to application software such that a doctor helps the treatment.

The MCU 50 may further be provided with a wired and/or wireless data communication interconnection module. A clock pulse source 53 and a radio frequency link 55 receive, from the CGM 45, data about glucose concentration in the body of the patient. If the CGM 45 is used, a Bluetooth ISM-band may be used to receive the signal. The CGM 45 provides the glucose concentration in the body of the patient. The MCU 50 has a CGM look-up table preset therein, for looking up the glucose concentration in the body of the patient and the input speed of insulin. The MCU 50 receives a signal sent by the CGM 45 connected thereto, and calculates an actually required infusion speed according to the CGM look-up table preset in the MCU 50. The MCU 50 has a comparison unit 47. The MCU 50 converts the rotation speed of the lead screw 22 to the insulin infusion speed, the comparison unit 47 compares the insulin infusion speed with the actually required infusion speed specified in the CGM look-up table according to the glucose concentration in the body of the patient, and the MCU 50 adjusts the rotation speed of the lead screw 22 according to the comparison result.

A multiplexer (mux) 25 is used to select the signal input to the ADC 23.

A real-time clock (RTC) 68 is used to record changes of a program in real time, and is also used to tell time and record time.

No matter how the device is mounted in the system, the power supply fluctuates, the temperature changes and the time elapses, the VREF 21 provides a fixed voltage.

A current limiter 33 connected to the MCU 50 limits an upper limit of the current used, to prevent short circuit or similar problems. A level converter 29 connected to the MCU 50 provides a conversion interface for elements using different voltages. A memory card 46 is a data storage device of an electronic flash memory for the current limiter 33 and the level converter 29 to use.

When a stepper motor is used, in addition to that the motor 52 itself has a function of adjusting the rotation speed of the motor, the MCU 50 may further use feedback to adjust and control the speed of the motor 52 through the motor controller 48 according to the signal of the magnetoresistive angle sensor 28, such that the infusion speed is more precise.

Figure 4:
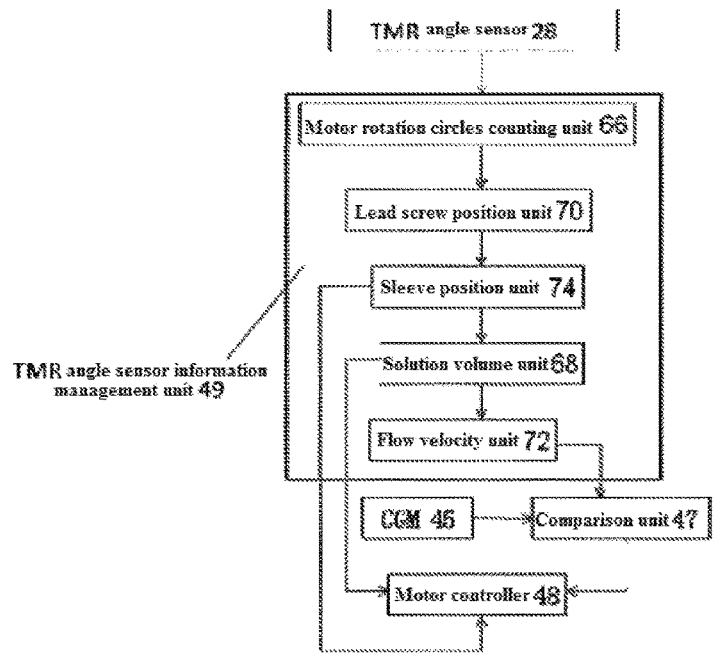
FIG. 4 is a principle diagram of a magnetoresistive sensor information management unit.

FIG. 4 shows the principle of a magnetoresistive angle sensor information management unit 49 in the MCU 50. The magnetoresistive angle sensor information management unit 49 comprises a motor rotation circle counting unit 66, a lead screw position unit 70, a sleeve position unit 74, a solution volume unit 68 and a flow velocity unit 72, and is preset with a conversion table of an infusion volume of the reservoir 4 to the position of the sleeve 8 within the reservoir 4, a conversion table of the position of the sleeve 8 of the reservoir 4 in the reservoir 4 to the position of the lead screw 22, and an algorithm of the rotation circles of the lead screw 22 to the position of the lead screw 22.

When the insulin pump 2 is used, it is necessary to calibrate the insulin pump. The MCU 50 can be used to calibrate the insulin pump 2, and can calculate the volume and speed of infusion. The lead screw 22 rotates, and the sleeve 8 moves accordingly. The motor rotation circles counting unit 66 records the rotation circles and time of the lead screw 22 according to the signal of the magnetoresistive angle sensor 28. According to the rotation circles of the lead screw 22 and the algorithm, preset in the MCU 50, of the rotation circles of the lead screw 22 to the position of the lead screw 22, Distance of linear movement of the lead screw=
(angle)*(longitudinal screw pitch)

the lead screw position unit 70 can calculate the position of the lead screw 22 or a linear distance of its movement in the Z-axis direction. Meanwhile, according to the conversion table of the position of the lead screw 22 to the position of the sleeve 8 in the reservoir 4, the sleeve position unit 74 may know the position of the sleeve 8 in the reservoir 4. Further, the solution volume unit 68 may know the volume of infusion or remaining liquid volume according to the conversion table of the diameter of the reservoir 4 to the position of the sleeve 8 thereof within the reservoir 4. The flow velocity unit 72 may calculate the speed of infusion according to the volume and time of infusion. If the conversion table of the rotation circles of the lead screw 22 to the infusion volume of the reservoir 4 is preset, the flow velocity unit 72 may record the rotation circles and time of the lead screw 22 according to the conversion table and the motor rotation circles counting unit 66, thereby calculating the speed of infusion more quickly. When the infusion speed deviates from a preset value too high or too low, the MCU 50 may instruct the motor controller 48 to adjust the rotation direction and speed of the motor 52. According to the position of the sleeve 8 in the reservoir 4 provided by the sleeve position unit 74 or according to the data of infusion volume provided by the solution volume unit 68, the MCU 50 may instruct the motor controller 48 to adjust the rotation direction and speed of the motor 52.

The calibration process of the insulin pump 2 is as follows: an empty reservoir 4 is placed on an injector pump 2, the magnetoresistive angle sensor information management unit 49 records the position of the sleeve 8 in the reservoir 4 detected by the magnetoresistive sensor 28, then, a liquid with a known volume is added to the reservoir 4, the volume value is input to the MCU 50, and the magnetoresistive angle sensor information management unit 49 can obtain a relation of the liquid volume with the position of the sleeve 8 in the reservoir 4 and a relation with the position of the lead screw 22, thereby calculating calibration parameters.

Figure 5:
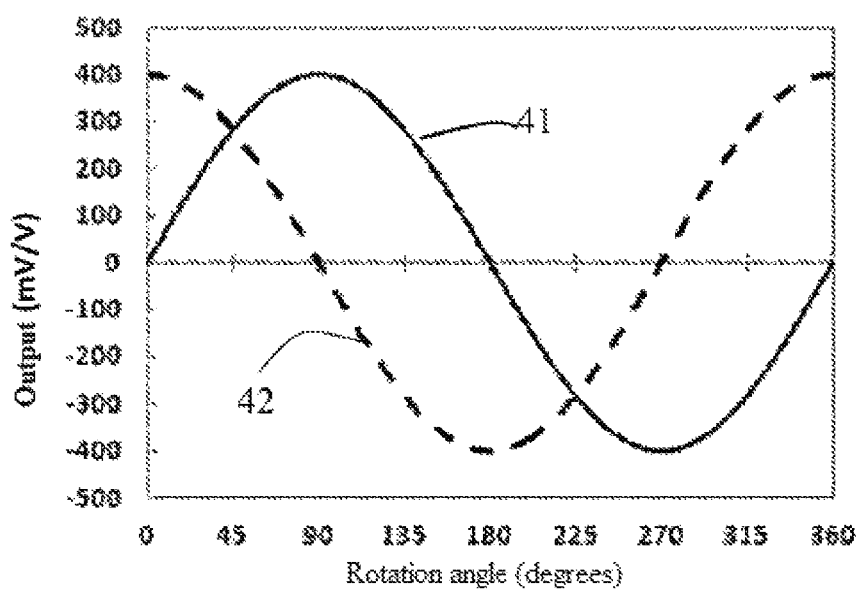
FIG. 5 is a conversion curve.

FIG. 5 is a conversion curve of the magnetoresistive angle sensor 28. When the permanent magnet 30 rotates with the lead screw 22 along a rotation direction 101, curves of X-axis and Y-axis magnetic field components changing along with the angle that are detected by the magnetoresistive angle sensor 28 are shown by the curves 41 and 42 in FIG. 4 respectively. The magnetoresistive angle sensor 28 converts the magnetic field amplitude generated by the permanent magnet 30 to an analog voltage signal, and the obtained analog voltage signal can be output directly or output after being converted to a digital signal by using an analog-to-digital conversion circuit (ADC). The angle of the permanent magnet 30, that is, the angle of the lead screw 22, may be known according to the output signal.

A method for manufacturing the above mini lead screw pump/insulin pump 2 is briefly described as follows: at least one permanent magnet 30 is mounted on a lead screw 22 such that it can rotate co-axially with the lead screw 22, and a magnetoresistive angle sensor 28 is mounted at a position within a unidirectional and saturated area in a magnetic field generated by the at least one permanent magnet 30; then, an MCU 50 for using feedback to control the rotation direction and speed of the lead screw 22 rotated by the motor 52 according to the signal of the magnetoresistive angle sensor 28 is mounted.

The above descriptions are merely preferred embodiments of the present invention, and are not intended to limit the present invention. For those skilled in the art, the present invention may have various modifications and changes, and the implementations in the present invention may also have different combinations and changes. Any modification, equivalent replacement, improvement or the like made without departing from the spirit and principle of the present invention shall all fall within the protection scope of the present invention.

The invention claimed is:

1. A mini lead screw pump mounted within a pump box, the mini lead screw pump comprising a motor, the motor driving a lead screw and a driving head connected to the lead screw, the lead screw configured to rotate in a nut and drive the driving head to move a sleeve in a reservoir, wherein the mini lead screw pump further comprises:
    at least one permanent magnet configured to rotate co-axially with the lead screw;
    a magnetoresistive angle sensor configured to sense a magnetic field generated by the at least one permanent magnet; and
    a micro control unit (MCU) configured to receive a signal of the magnetoresistive angle sensor and control a rotation direction and speed of the lead screw according to the signal of the magnetoresistive angle sensor.

2. The mini lead screw pump according to claim 1, wherein the magnetoresistive angle sensor includes: a biaxial rotary magnetic sensor; two orthogonal uniaxial magnetic angle sensors; or a uniaxial or biaxial linear magnetic sensor.

3. The mini lead screw pump according to claim 1, wherein the magnetoresistive angle sensor includes an AMR, a GMR or a TMR sensor.

4. The mini lead screw pump according to claim 1, wherein a central axis of the permanent magnet and a central axis of the lead screw pass through a center of the magnetoresistive angle sensor.

5. The mini lead screw pump according to claim 1, wherein the at least one permanent magnet includes a one-piece permanent magnet or a split-type permanent magnet, and is disc-shaped, ring-shaped or square-shaped.

6. The mini lead screw pump according to claim 1, wherein the at least one permanent magnet is two permanent magnets, each of the permanent magnets has multiple different magnetic poles, and the two permanent magnets are located at two ends of the lead screw respectively or disposed at the same end of the lead screw as a string.

7. The mini lead screw pump according to claim 1, wherein the MCU is configured to control the rotation direction and speed of the motor through a motor controller.

8. The mini lead screw pump according to claim 7, wherein the MCU comprises a magnetoresistive sensor information management unit comprising:
 a motor angle counting unit configured to monitor the angle of the motor,
 at least one of a lead screw position unit configured to calculate a linear movement position of the lead screw or a sleeve position unit configured to calculate a position of the sleeve in the reservoir,
 a solution volume unit configured to calculate a volume of a solution in the reservoir, and
 a flow velocity unit configured to convert a rotation speed of the lead screw to an infusion speed of the reservoir.

9. The mini lead screw pump according to claim 1, wherein the MCU has a wired and/or wireless data communication interconnecting function.

10. The mini lead screw pump according to claim 1, wherein the MCU is configured to receive a signal sent by a continuous glucose monitor (CGM) connected thereto, and calculates a required infusion speed according to a CGM look-up table preset in the MCU.

11. The mini lead screw pump according to claim 10, wherein the mini lead screw pump comprises a comparison unit configured to provide comparison data feedback by comparing an infusion speed of the mini lead screw pump with the required infusion speed, and the MCU is configured to adjust the speed of the lead screw according to comparison data feedback.

12. The mini lead screw pump according to claim 1, wherein the motor is a DC motor or a stepper motor.

13. The mini lead screw pump according to claim 1, wherein the mini lead screw pump comprises a transmission device connecting the motor and the lead screw.

14. The mini lead screw pump according to claim 1, wherein the mini lead screw pump comprises a slideway or a guide rod, the slideway or guide rod is parallel to the lead screw, and the driving head is configured to slide within the slideway or slide along the guide rod.

15. The mini lead screw pump according to claim 1, comprising an anti-backlash device located on the lead screw.

16. A method for manufacturing the mini lead screw pump according to claim 1, the mini lead screw pump comprising a lead screw and a driving head connected to the lead screw, and the lead screw rotating clockwise or counterclockwise, thereby driving the driving head to push a sleeve to move in a reservoir, wherein the method comprises:
 mounting at least one permanent magnet on the lead screw such that it is rotatable co-axially with the lead screw, and mounting a magnetoresistive angle sensor at a position within a unidirectional and saturated area of a magnetic field generated by the at least one permanent magnet; and
 operably connecting a micro control unit (MCU) to receive a signal from the magnetoresistive angle sensor, wherein the MCU is configured to control a rotation direction and speed of the lead screw according to the received signal from the magnetoresistive angle sensor.

17. The method for manufacturing a mini lead screw pump according to claim 16, wherein the magnetoresistive angle sensor is an AMR, a GMR or a TMR sensor.

18. The method for manufacturing a mini lead screw pump according to claim 16, wherein the MCU is configured to receive a signal sent by a continuous glucose monitor (CGM) and calculate an infusion speed according to a look-up table in the MCU.

19. A mini lead screw pump, comprising:
 a reservoir;
 a sleeve configured to move in the reservoir;
 a lead screw;
 a driving head connected to the lead screw;
 a motor configured to rotate the lead screw to drive the driving head to move the sleeve in the reservoir;
 at least one permanent magnet configured to rotate co-axially with the lead screw;
 a magnetoresistive angle sensor configured to sense a magnetic field generated by the at least one permanent magnet, wherein the magnetoresistive angle sensor includes an AMR, a GMR or a TMR sensor, wherein a central axis of the permanent magnet and a central axis of the lead screw pass through a center of the magnetoresistive angle sensor; and
 a micro control unit (MCU) configured to receive a signal of the magnetoresistive angle sensor and use a motor controller to control a rotation direction and speed of the lead screw based on the signal of the magnetoresistive angle sensor.

20. The mini lead screw pump of claim 19, wherein:
 the MCU is configured to receive a signal sent by a continuous glucose monitor (CGM), and calculate a required infusion speed according to a CGM look-up table preset in the MCU; and
 the MCU comprises a magnetoresistive sensor information management unit configure to:
 monitor the angle of the motor,
 calculate a linear movement position of the lead screw or calculate a position of the sleeve in the reservoir,
 calculate a volume of a solution in the reservoir, and
 convert a rotation speed of the lead screw to an infusion speed of the reservoir.

* * * * *